(12) United States Patent
Makriyannis et al.

(10) Patent No.: US 7,820,144 B2
(45) Date of Patent: Oct. 26, 2010

(54) RECEPTOR SELECTIVE CANNABIMIMETIC AMINOALKYLINDOLES

(75) Inventors: Alexandros Makriyannis, Watertown, MA (US); Hongfeng Deng, Acton, MA (US)

(73) Assignee: University of Connecticut, Farmington, CT (US)

( * ) Notice: Subject to any disclaimer, the term of this patent is extended or adjusted under 35 U.S.C. 154(b) by 744 days.

(21) Appl. No.: 11/620,248

(22) Filed: Jan. 5, 2007

(65) Prior Publication Data

US 2007/0243134 A1 Oct. 18, 2007

Related U.S. Application Data

(63) Continuation-in-part of application No. 10/470,359, filed as application No. PCT/US02/02501 on Jan. 29, 2002, now Pat. No. 7,173,027.

(60) Provisional application No. 60/264,855, filed on Jan. 29, 2001.

(51) Int. Cl.
*A61B 5/055* (2006.01)

(52) U.S. Cl. .................... 424/9.37; 424/1.11; 424/1.65; 424/1.81; 424/1.85; 424/1.89; 424/9.1; 424/9.3

(58) Field of Classification Search ................ 424/1.11, 424/1.65, 1.81, 1.85, 1.89, 9.1, 9.3, 9.37, 424/9.4, 9.45, 9.451, 9.5, 9.6, 9.7, 9.8; 548/400, 548/950; 546/1, 152, 184, 249; 544/1, 224
See application file for complete search history.

(56) References Cited

U.S. PATENT DOCUMENTS 6,900,236 B1 * 5/2005 Makriyannis et al. ....... 514/415
7,173,027 B2 * 2/2007 Makriyannis et al. ..... 514/235.2

* cited by examiner

*Primary Examiner*—D L Jones
(74) *Attorney, Agent, or Firm*—Alix, Yale & Ristas, LLP

(57) ABSTRACT

Disclosed are cannabimimetic aminoalkylindole compounds and methods for their manufacture. The disclosed compounds are surprisingly potent and selective cannabinoids. The disclosed compounds may include radioactive atoms. Also disclosed are methods of using the disclosed compounds, including use of the disclosed compounds to stimulate a cannabinoid receptor, to provide a physiological effect in an animal or individual, to treat a condition in an animal or individual and for use in radioimaging.

20 Claims, No Drawings

RECEPTOR SELECTIVE CANNABIMIMETIC AMINOALKYLINDOLES

CROSS REFERENCE TO RELATED APPLICATIONS

This application is a continuation-in-part of U.S. application Ser. No. 10/470,359 filed Jul. 24, 2003 which is the United States National Stage Application of International Patent Application No. PCT/US02/02501, filed on Jan. 29, 2002, which claims the benefit of U.S. Provisional Application No. 60/264,855, filed Jan. 29, 2001, the contents of each of which are incorporated by reference in their entirety.

FIELD

The present disclosure relates generally to indole compounds exhibiting cannabimimetic activity. The present disclosure is more particularly concerned with new and improved aminoalkylindole compounds exhibiting high binding affinity for at least one cannabinoid receptor and/or high selectivity for one cannabinoid receptor, pharmaceutical preparations employing these compounds and methods of administering therapeutically effective amounts of these compounds to provide a physiological effect.

BACKGROUND

Classical cannabinoids such as the marijuana derived cannabinoid $\Delta^9$-tetrahydrocannabinol, ($\Delta^9$-THC) produce their pharmacological effects through interaction with specific cannabinoid receptors in the body. So far, two cannabinoid receptors have been characterized: CB1, a central receptor found in the mammalian brain and peripheral tissues and CB2, a peripheral receptor found only in the peripheral tissues. Compounds that are agonists or antagonists for one or both of these receptors have been shown to provide a variety of pharmacological effects.

There is considerable interest in developing cannabimimetic compounds possessing high affinity for one of the CB1 or CB2 receptors. Such compounds may offer a rational therapeutic approach to a variety of disease conditions. One class of cannabimimetic compound encompasses indole derivatives such as the well-known aminoalkylindoles represented by WIN 55212-2 {(R)-(+)-[2,3-dihydro-5-methyl-3-[(4-morpholinyl)methyl]-pyrrolo[1,2,3-de]-1,4-benzoxazin-6-yl](1-naptha-lenyl)methanone}. Aminoalkylindoles of this type typically have a carbon linked alkylheterocyclic substituent at the indole-1 position, which is believed to be important for their cannabimimetic activities. These known materials are not selective for preferential activation of one of the CB1 or CB2 receptors.

SUMMARY

It has now been found that certain aminoalkylindoles possess surprising cannabimimetic properties, including selectivity for the CB1 or CB2 cannabinoid receptor. Broadly, in one aspect of the disclosure the novel cannabimimetic compounds can be represented by the structural formula I below, physiologically acceptable salts, diasteromers, enantiomers, double bond isomers or mixtures thereof.

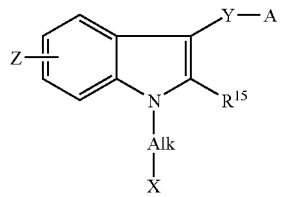

structural formula 1 wherein:
Z comprises at least one substituent independently chosen from hydrogen; halogen; CN; $CF_3$; hydroxy; alkoxy; thioalkoxy; aryl and lower alkyl;
Alk comprises an alkyl group or a substituted alkyl group;
X comprises $NHSO_2R^5$, a 5, 6 or 7 member heterocyclic ring, including at least one heteroatom independently selected from oxygen, nitrogen and sulfur; a substituted 5, 6 or 7 member heterocyclic ring, including at least one heteroatom independently selected from oxygen, nitrogen and sulfur; a bicyclic ring; or a bicyclic ring including at least one heteroatom independently selected from oxygen, nitrogen and sulfur;
$R^5$ comprises alkyl, halogenated alkyl and fluorinated alkyl;
R comprises hydrogen, CN, CHO, alkyl, halogenated alkyl, fluorinated alkyl or a substituted alkyl group;
Y comprises carbonyl, CH=CH (cis or trans), CONH or C=NH; and
A comprises alkyl, $COCF_3$, adamantyl; azoadamantyl; cycloalkyl; phenyl; naphthyl; 9-anthracenyl; pyridinyl; quinolinyl; isoquinolinyl; quinazolinyl; an aliphatic bicyclic ring; an azabicyclic ring; a heterobicyclic ring; any of the above with one or more substituents independently selected from amino, halogen, hydroxy, nitro, nitroso, azido, isothiocyanato, cyano, COOH, alkyl, $CONR^3R^4$ where $R^3$ and $R^4$ each independently comprise H, alkyl or substituted alkyl, $NCOR^3R^4$ where $R^3$ and $R^4$ each independently comprise H, alkyl, substituted alkyl, $CF_3$, $SO_2NR^3R^4$ where $R^3$ and $R^4$ each independently comprise H, alkyl, substituted alkyl or $CF_3$; or a salt of any of the above.

In one aspect of the disclosure the compounds can be represented by structural formula I above, wherein:
Z comprises hydrogen;
Alk comprises a $C_{1-2}$alkyl group;
X comprises a 5, 6 or 7 member heterocyclic ring, including at least one heteroatom independently selected from oxygen, nitrogen and sulfur; a substituted 5, 6 or 7 member heterocyclic ring, including at least one heteroatom independently selected from oxygen, nitrogen and sulfur; a bicyclic ring; or a bicyclic ring including at least one heteroatom independently selected from oxygen, nitrogen and sulfur;
R comprises hydrogen;
Y comprises carbonyl; and
A comprises alkyl, $COCF_3$, adamantyl; azoadamantyl; phenyl; naphthyl; 9-anthracenyl; pyridinyl; quinolinyl; isoquinolinyl; quinazolinyl; an aliphatic bicyclic ring; an azabicyclic ring; any of the above with one or more substituents independently selected from amino, halogen, hydroxy, nitro, nitroso, azido, isothiocyanato, cyano, COOH, alkyl, $CONR^3R^4$ where $R^3$ and $R^4$ each independently comprise H, alkyl or substituted alkyl, $NCOR^3R^4$ where $R^3$ and $R^4$ each independently comprise H, alkyl, substituted alkyl, $CF_3$, $SO_2NR^3R^4$ where $R^3$ and $R^4$ each independently comprise H, alkyl, substituted alkyl or $CF_3$; or a salt of any of the above.

In one aspect of the disclosure the compounds can be represented by structural formula I above, wherein:
Z comprises hydrogen, I, F, CN or CF3 in any possible position or alkoxy in the 7 position;
Alk comprises a $CH_2$;

X comprises a piperidinyl ring with a CH₃ group attached to the first ring carbon atom or a morpholinyl ring with a CH₃ group attached to the first ring carbon atom or a morpholinyl ring;

R comprises hydrogen or $CH_3$;

Y comprises C=O or CONH; and

A comprises alkyl, $COCF_3$, adamantyl; azoadamantyl; phenyl; naphthyl; 9-anthracenyl; pyridinyl; quinolinyl; isoquinolinyl; quinazolinyl; an aliphatic bicyclic ring; an azabicyclic ring; any of the above with one or more substituents independently selected from amino, halogen, hydroxy, nitro, nitroso, azido, isothiocyanato, cyano, COOH, alkyl, $CONR^3R^4$ where $R^3$ and $R^4$ each independently comprise H, alkyl or substituted alkyl, $NCOR^3R^4$ where $R^3$ and $R^4$ each independently comprise H, alkyl, substituted alkyl, $CF_3$, $SO_2NR^3R^4$ where $R^3$ and $R^4$ each independently comprise H, alkyl, substituted alkyl or $CF_3$; or a salt of any of the above.

In another aspect of the disclosure the compounds can be represented by structural formula II below,

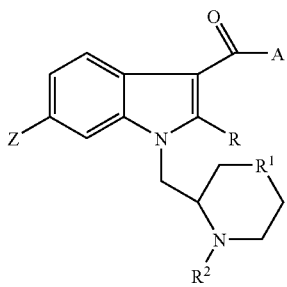

structural formula II wherein:

Z comprises hydrogen;

R comprises hydrogen;

$R^1$ comprises N, O, S or $CH_2$;

$R^2$ comprises H, alkyl, $CF_3$, $CH_2C\equiv CH$, $CH_2CH\equiv CH_2$ or $CH_2Ph$; and A comprises alkyl, $COCF_3$, adamantyl; azoadamantyl; phenyl; naphthyl; 9-anthracenyl; pyridinyl; quinolinyl; isoquinolinyl; quinazolinyl; an aliphatic bicyclic ring; an azabicyclic ring; any of the above with one or more substituents independently selected from amino, halogen, hydroxy, nitro, nitroso, azido, isothiocyanato, cyano, COOH, alkyl, $CONR^3R^4$ where $R^3$ and $R^4$ each independently comprise H, alkyl or substituted alkyl, $NCOR^3R^4$ where $R^3$ and $R^4$ each independently comprise H, alkyl, substituted alkyl, $CF_3$, $SO_2NR^3R^4$ where $R^3$ and $R^4$ each independently comprise H, alkyl, substituted alkyl or $CF_3$; or a salt of any of the above.

Unless otherwise specifically defined, "acyl" refers to the general formula —C(O)alkyl.

Unless otherwise specifically defined, "acyloxy" refers to the general formula —O-acyl.

Unless otherwise specifically defined, "alcohol" refers to the general formula alkyl-OH and includes primary, secondary and tertiary variations.

Unless otherwise specifically defined, "alkyl" or "lower alkyl" refers to a linear, branched or cyclic alkyl group, having from 1 to about 16 carbon atoms and advantageously having from 1 to about 9 carbon atoms. The alkyl group can be saturated or unsaturated. The alkyl group can be unsubstituted, singly substituted or, if possible, multiply substituted, with substituent groups in any possible position. Alkyl groups include, for example, methyl, ethyl, propyl, butyl, hexyl, octyl, isopropyl, isobutyl, tert-butyl, cyclopropyl, tetramethylcyclopropyl, cyclohexyl, cyclooctyl, vinyl and allyl. Unless otherwise specifically limited, a cyclic alkyl group includes monocyclic, bicyclic, tricyclic and polycyclic rings, for example norbornyl, adamantyl and related terpenes.

Unless otherwise specifically defined, "alkoxy" refers to the general formula —O-alkyl.

Unless otherwise specifically defined, "alkylmercapto" refers to the general formula —S-alkyl.

Unless otherwise specifically defined, "alkylamino" refers to the general formula —(NH)-alkyl.

Unless otherwise specifically defined, "di-alkylamino" refers to the general formula —N(alkyl)₂. Unless otherwise specifically limited di-alkylamino includes cyclic amine compounds such as piperidine and morpholine.

Unless otherwise specifically defined, an aromatic ring is an unsaturated ring structure, advantageously having about 4 to about 7 ring members, and including only carbon as ring atoms. The aromatic ring structure can be unsubstituted, singly substituted or, if possible, multiply substituted, with substituent groups in any possible position.

Unless otherwise specifically defined, "aryl" refers to an aromatic ring system that includes only carbon as ring atoms, for example phenyl, biphenyl or naphthyl. The aryl group can be unsubstituted, singly substituted or, if possible, multiply substituted, with substituent groups in any possible position.

Unless otherwise specifically defined, "aroyl" refers to the general formula —C(=O)-aryl.

Unless otherwise specifically defined, a bicyclic ring structure comprises 2 fused or bridged rings, advantageously having about 6 to about 12 ring atoms, that include only carbon as ring atoms. The bicyclic ring structure can be saturated or unsaturated. The bicyclic ring structure can be unsubstituted, singly substituted or, if possible, multiply substituted, with substituent groups in any possible position. The individual rings may or may not be of the same type. Examples of bicyclic ring structures include, Dimethyl-bicyclo[3,1,1]heptane, bicyclo[2,2,1]heptadiene, decahydro-naphthalene, bicyclohexane, bicyclooctane and bicyclodecane.

Unless otherwise specifically defined, a carbocyclic ring is a non-aromatic ring structure, saturated or unsaturated, advantageously having about 3 to about 8 ring members, that includes only carbon as ring atoms, for example, cyclohexadiene or cyclohexane. The carbocyclic ring can be unsubstituted, singly substituted or, if possible, multiply substituted, with substituent groups in any possible position.

Unless otherwise specifically defined, "halogen" refers to an atom selected from fluorine, chlorine, bromine and iodine.

Unless otherwise specifically defined, a heteroaromatic ring is an unsaturated ring structure, advantageously having about 4 to about 8 ring members, that has carbon atoms and one or more heteroatoms, including oxygen, nitrogen and/or sulfur, as ring atoms, for example, pyridine, furan, quinoline, and their derivatives. The heteroaromatic ring can be unsubstituted, singly substituted or, if possible, multiply substituted, with substituent groups in any possible position.

Unless otherwise specifically defined, a heterobicyclic ring structure comprises 2 fused or bridged rings, advantageously having about 6 to about 12 ring atoms, including carbon and one or more heteroatoms, including oxygen, nitrogen and/or sulfur, as ring atoms. The heterobicyclic ring structure is saturated or unsaturated. The heterobicyclic ring can be unsubstituted, singly substituted or, if possible, multiply substituted, with substituent groups in any possible position. The individual rings may or may not be of the same type. Examples of heterobicyclic ring structures include tropane, quinuclidine and tetrahydro-benzofuran.

Unless otherwise specifically defined, a heterocyclic ring is a saturated or unsaturated ring structure, advantageously having about 3 to about 8 ring members, that has carbon atoms and one or more heteroatoms, including oxygen, nitrogen and/or sulfur, as ring atoms, for example, piperidine, morpholine, piperazine, pyrrolidine, thiomorpholine, tetrahydropyridine, and their derivatives. The heterocyclic ring can be unsubstituted, singly substituted or, if possible, multiply substituted, with substituent groups in any possible position.

Unless otherwise specifically defined, a heterotricyclic ring structure comprises 3 rings that may be fused, bridged or both fused and bridged, and that include carbon and one or more heteroatoms, including oxygen, nitrogen and/or sulfur, as ring atoms. The heterotricyclic ring structure can be saturated or unsaturated. The heterotricyclic ring structure can be unsubstituted, singly substituted or, if possible, multiply substituted, with substituent groups in any possible position. The individual rings may or may not be of the same type. Examples of heterotricyclic ring structures include 2,4,10-trioxaadamantane, tetradecahydro-phenanthroline.

Unless otherwise specifically defined, a heteropolycyclic ring structure comprises more than 3 rings that may be fused, bridged or both fused and that include carbon and one or more heteroatoms, including oxygen, nitrogen and/or sulfur, as ring atoms. The heteropolycyclic ring structure can be saturated or unsaturated. The heteropolycyclic ring structure can be unsubstituted, singly substituted or, if possible, multiply substituted, with substituent groups in any possible position. The individual rings may or may not be of the same type. Examples of heteropolycyclic ring structures include azaadamantine, 5-norbornene-2,3-dicarboximide.

Unless otherwise specifically defined, the term "phenacyl" refers to the general formula -phenyl-acyl.

Unless otherwise specifically defined, a polycyclic ring structure comprises more than 3 rings that may be fused, bridged or both fused and bridged, and that includes carbon as ring atoms. The polycyclic ring structure can be saturated or unsaturated. The polycyclic ring structure can be unsubstituted, singly substituted or, if possible, multiply substituted, with substituent groups in any possible position. The individual rings may or may not be of the same type. Examples of polycyclic ring structures include adamantine, bicyclooctane, norbornane and bicyclononanes.

Unless otherwise specifically defined, a spirocycle refers to a ring system wherein a single atom is the only common member of two rings. A spirocycle can comprise a saturated carbocyclic ring comprising about 3 to about 8 ring members, a heterocyclic ring comprising about 3 to about 8 ring atoms wherein up to about 3 ring atoms may be N, S, or O or a combination thereof.

Unless otherwise specifically defined, a tricyclic ring structure comprises 3 rings that may be fused, bridged or both fused and bridged, and that includes carbon as ring atoms. The tricyclic ring structure can be saturated or unsaturated. The tricyclic ring structure can be unsubstituted, singly substituted or, if possible, multiply substituted, with substituent groups in any possible position, and may be substituted or unsubstituted. The individual rings may or may not be of the same type. Examples of tricyclic ring structures include fluorene and anthracene.

Unless otherwise specifically limited the term substituted means substituted by a below-described substituent group in any possible position. Substituent groups for the above moieties useful in this disclosure are those groups that do not significantly diminish the biological activity of the disclosed compound. Unless otherwise specifically limited a substituent group or a substituent group that does not significantly diminish the biological activity of the disclosed compound includes, for example, H, halogen, $N_3$, NCS, CN, $NO_2$, $NX_1X_2$, $OX_3$, $C(X_3)_3$, OAc, O-acyl, O-aroyl, NH-acyl, NH-aroyl, NHCOalkyl, CHO, C(halogen)$_3$, COC(halogen)$_3$, $COOX_3$, $SO_3H$, $PO_3H_2$, $SO_2NX_1X_2$, $CONX_1X_2$, $NCOX_1X_2$, alkyl, substituted alkyl, phenyl, substituted phenyl, alcohol, alkoxy, alkylmercapto, alkylamino, di-alkylamino, sulfonamide or thioalkoxy (wherein $X_1$ and $X_2$ each independently comprise H, alkyl or substituted alkyl, or $X_1$ and $X_2$ together comprise part of a heterocyclic ring having about 4 to about 7 ring members and optionally one additional heteroatom selected from O, N or S, or $X_1$ and $X_2$ together comprise part of an imide ring having about 5 to about 6 members and $X_3$ comprises H, alkyl, loweralkylhydroxy, or alkyl-$NX_1X_2$), $NCOR^3R^4$ (where $R^3$ and $R^4$ each independently comprise H, alkyl, substituted alkyl, $CF_3$) or $SO_2NR^3R^4$ (where $R^3$ and $R^4$ each independently comprise H, alkyl, substituted alkyl or $CF_3$, sulfonamide, or lower alcohol). Unless otherwise specifically limited, a substituent group may be in any possible position.

An isotope is one of two or more species of the same element. Each isotope of an element will have the same number of protons in its nucleus, the same atomic number and the same position in the Periodic Table. However each isotope of that element will have a different number of neutrons in its nucleus and therefore a different mass than other isotopes of that species. The term nuclide is sometimes used synonymously with the term isotope. As used herein a natural isotope has an atomic mass corresponding most closely with the atomic mass shown for that element in the Periodic Table. As used herein an unnatural isotope has an atomic mass that is further removed from the atomic mass shown for that element in the Periodic Table than the natural isotope. For example, protium (hydrogen-1 or $^1H$) is the natural isotope of hydrogen and deuterium (hydrogen-2 or $^2H$) and tritium (hydrogen-3 or $^3H$) are all unnatural isotopes of hydrogen. The compounds of the present disclosure can comprise isotopes at one or more of their atoms. For example, the compounds can be radiolabeled with isotopes, such as tritium, carbon-11, carbon-13, carbon-14, oxygen-15, nitrogen-15, oxygen-18, fluorine-18, bromine-76, bromine-77, bromine-82, iodine-123 or iodine-125. The present disclosure encompasses all isotopic variations of the described compounds, whether natural or unnatural, radioactive or not.

In general, unless otherwise explicitly stated the disclosed materials may be alternately formulated to comprise, consist of, or consist essentially of, any appropriate components or moieties herein disclosed. The disclosed materials may additionally, or alternatively, be formulated so as to be devoid, or substantially free, of any components, materials, ingredients, adjuvants moieties or species used in the prior art compositions or that are otherwise not necessary to the achievement of the function and/or objective of the present disclosure.

When the word "about" is used herein it is meant that the amount or condition it modifies can vary some beyond the stated amount so long as the function and/or objective of the disclosure are realized. The skilled artisan understands that there is seldom time to fully explore the extent of any area and expects that the disclosed result might extend, at least somewhat, beyond one or more of the disclosed limits. Later, having the benefit of this disclosure and understanding the concept and embodiments disclosed herein, a person of ordinary skill can, without undue effort, explore beyond the disclosed limits and, when embodiments are found to be without any unexpected characteristics, those embodiments are within the meaning of the term about as used herein.

Some of the disclosed cannabinoid compounds exhibit high affinity for the CB1 and/or CB2 cannabinoid receptor. More specifically, some analogs showed similar or higher receptor binding affinity than the well-known indole cannabinoid WIN 55212-2. Thus, another aspect of the disclosure is use of at least one disclosed compound to interact with a cannabinoid receptor.

Some of the disclosed cannabinoid compounds show a surprisingly higher selectivity for one of the CB1 or CB2 cannabinoid receptors. These selective compounds are able to interact with one cannabinoid receptor, for example the CB2 receptor, without affecting the CB1 cannabinoid receptor to the same degree. More specifically, some of these compounds show not only comparable cannabimimetic activity with the compound WIN 55212-2, but also a surprisingly higher selectivity for one of the CB1 or CB2 receptors. Therefore, another aspect of the disclosure is use of at least one disclosed compound to preferentially interact with one cannabinoid receptor.

Some of the disclosed cannabinoid compounds can act as high affinity modulators for the CB2 cannabinoid receptor. The disclosed cannabinoid compounds therefore are potential therapeutic agents through the modulation of a cannabinoid receptor.

Some of the cannabinoid compounds described herein may be agonists for at least one of the cannabinoid receptors. The disclosed cannabinoid agonists interact with the at least one cannabinoid receptor binding site to initiate a physiological or a pharmacological response characteristic of that receptor. Therefore, a further aspect of the disclosure is use of at least one disclosed compound to initiate an agonistic response from a cannabinoid receptor.

Some of the compounds described herein may be cannabinoid receptor antagonists. The cannabinoid antagonists interact with the CB1 and/or CB2 cannabinoid receptor binding site to block other ligands from the receptor binding site without initiating a physiological or a pharmacological response characteristic of that receptor. Thus, cannabinoid antagonists typically oppose the cannabinoid receptor site response characteristics initiated by cannabinoid agonists. Therefore, an aspect of the disclosure is use of at least one disclosed compound to oppose initiation of an agonistic response from a cannabinoid receptor.

The disclosed cannabinoid compounds described herein, and physiologically acceptable salts thereof, have pharmacological properties when administered in therapeutically effective amounts for providing a physiological response in individuals and/or animals. Thus, another aspect of the disclosure is the administration of a therapeutically effective amount of at least one disclosed cannabimimetic compound, or a physiologically acceptable salt thereof, to an individual or animal to provide a physiological response.

Some of the halogen containing analogs, for example those analogs comprising iodide and fluoride, are potential radioactive probes for imaging in vivo the distribution of cannabinoid receptors.

Some of the radioactive isotope containing analogs have potential as radiopharmaceutical analogs (disclosed analogs that have been labeled with radioactive isotopes). These radiopharmaceuticals can be administered to patients and the emitted radiation can be measured. The majority of these diagnostic tests involve the formation of an image using a camera suitable to detect the emitted radiation. Positron emission tomography (PET) is one nuclear medicine tomographic imaging technique, which produces a three-dimensional image or map of functional processes in a patient's body. To conduct the PET scan, a short-lived radiopharmaceutical analog that decays by emitting a positron is administered into the subject (usually by injection into the blood stream). There is a waiting period while the radiopharmaceutical analog becomes concentrated in tissues of interest such as a cannabinoid receptor. After the waiting period the patient is placed in an imaging scanner. The scanner collects multiple images and a computer is used to apply an algorithm to the multiple images and provide a three dimensional image. Single photon emission computed tomography (SPECT) is another nuclear medicine tomographic imaging technique. To conduct the SPECT scan, a short-lived radiopharmaceutical analog that decays to produce a gamma ray is administered into the subject. There is a waiting period while the radiopharmaceutical analog becomes concentrated in tissues of interest such as a cannabinoid receptor. After the waiting period the patient is placed in an imaging scanner and SPECT imaging is performed by using a gamma camera to acquire multiple two dimensional images from multiple angles. A computer is then used to apply an algorithm to the multiple images to provide a three dimensional image.

A better understanding of the disclosure will be obtained from the following detailed description of the article and the desired features, properties, characteristics, and the relation of the elements as well as the process steps, one with respect to each of the others, as set forth and exemplified in the description and illustrative embodiments.

DETAILED DESCRIPTION

As used herein, a "therapeutically effective amount" of a compound, is the quantity of a compound which, when administered to an individual or animal, results in a sufficiently high level of that compound in the individual or animal to cause a discernible increase or decrease in stimulation of cannabinoid receptors. Such discernible increase or decrease in stimulation of cannabinoid receptors can provide a physiological effect in the individual or animal.

Physiological effects that result from CB1 cannabinoid receptor interaction with agonist compounds include relief of pain, peripheral pain, neuropathic pain, glaucoma, epilepsy and nausea such as associated with cancer chemotherapy; appetite enhancement; selective killing of glioma and breast cancer cells; alleviation of the symptoms of neurodegenerative diseases including Multiple Sclerosis, Parkinson's Disease, Huntington's Chorea and Alzheimer's Disease, reduction of fertility; prevention or reduction of diseases associated with motor function such as Tourette's syndrome; neuroprotection; suppression of memory and peripheral vasodilation. Physiological effects that result from CB1 cannabinoid receptor interaction with antagonist compounds include appetite suppression; memory enhancement; beneficial effects in mental disorders such as schizophrenia and depression; and beneficial effects in endotoxic and hypotensive shock. Physiological effects that result from CB2 cannabinoid receptor interaction with agonist compounds include relief of pain, peripheral pain, neuropathic pain, glaucoma, epilepsy and nausea such as associated with cancer chemotherapy; selective killing of glioma and breast cancer cells; alleviation of the symptoms of neurodegenerative diseases including Multiple Sclerosis, Parkinson's Disease, Huntington's Chorea and Alzheimer's Disease, reduction of fertility; prevention or reduction of diseases associated with motor function such as Tourette's syndrome; prevention or reduction of inflammation; neuroprotection; and suppression of the immune system. Physiological effects that result from CB2 cannabinoid receptor interaction with antagonist compounds include enhancement of the immune system and peripheral vasoconstriction. Typically a "therapeutically effective amount" of the novel compounds ranges from about 10 mg/day to about 1,000 mg/day.

As used herein, an "individual" refers to a human. An "animal" refers to, for example, veterinary animals, such as dogs, cats, horses and the like, and farm animals, such as cows, pigs and the like.

The compounds of the present disclosure can be administered by a variety of known methods, including orally, rectally, or by parenteral routes (e.g., intramuscular, intravenous, subcutaneous, nasal or topical). The form in which the compounds are administered will be determined by the route of administration. Such forms include, but are not limited to, capsular and tablet formulations (for oral and rectal administration), liquid formulations (for oral, intravenous, intramuscular or subcutaneous administration) and slow releasing microcarriers (for rectal, intramuscular or intravenous administration). The formulations can also comprise one or more of a physiologically acceptable excipient, vehicle and optional adjuvants, flavorings, colorants and preservatives. Suitable physiologically to acceptable vehicles may include, for example, saline, sterile water, Ringer's solution, and isotonic sodium chloride solutions. The specific dosage level of compound will depend upon a number of factors, including, for example, biological activity of the particular preparation, age, body weight, sex and general health of the individual being treated.

The following examples are given for purposes of illustration only in order that the present disclosure may be more fully understood. These examples are not intended to limit in any way the scope of the disclosure unless otherwise specifically indicated.

The prepared cannabimimetic indole derivatives can generally be described with reference to exemplary structural formulas 1 and 2 below.

The compounds of exemplary structural formula 1 include both racemics and two enantiomers. Some compounds are listed in TABLE 1.

Exemplary Structural Formula 1

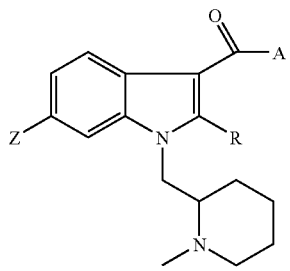

It should be noted that alk-X for all of the materials of TABLE 1 was 1-(N-methyl-2-piperidinyl)methyl.

TABLE 1

|  |  |  |  | $K_i$ nM |  |
|---|---|---|---|---|---|
| analog | Z | R | A | CB1 | CB2 |
| 2-7(R,S) | H | H | 2-iodo-5-nitrophenyl | 403 | 5.7 |
| 2-7(R) | H | H | 2-iodo-5-nitrophenyl | 285 | 0.53 |
| 2-7(S) | H | H | 2-iodo-5-nitrophenyl | 906 | 9.5 |
| 2-7(R,S) human | H | H | 2-iodo-5-nitrophenyl |  | 1.6 |
| 2-24(R) | H | H | 2-iodophenyl | 1.8 | 2.1 |
| 2-24(S) | H | H | 2-iodophenyl | 561 | 583 |

Surprisingly, and as exemplified by compounds 2-7 and 2-24, in all cases the + configuration (R configuration) has a higher selectivity for the CB2 receptor and a higher affinity for the CB2 receptor.

Compound 2-7 was tested for binding affinity to human CB2 receptors using the below-described procedure with human tissue samples. That compound was found to be a surprisingly potent cannabinoid.

Exemplary Structural Formula 2

TABLE 2

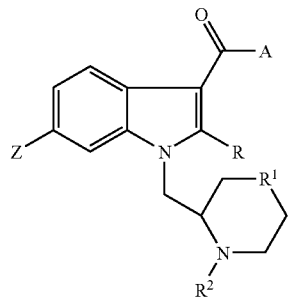

|  |  |  |  |  |  | Ki nM |  |
|---|---|---|---|---|---|---|---|
| analog | Z | R | $R^1$ | $R^2$ | A | CB1 | CB2 |
| 2-25 | H | H | O | CH$_2$Ph | 2-iodo-6-methylphenyl | 1217 | 1800 |
| 2-26 | H | H | O | CH$_2$Ph | 4-iodo-3-methyl-nitrophenyl | 4212 | 1431 |
| 2-27 | H | H | O | CH$_2$Ph | 2-iodo-3-methyl-nitrophenyl | 2383 | 927.5 |

TABLE 2-continued

| analog | Z | R | R¹ | R² | A | Ki nM CB1 | Ki nM CB2 |
|---|---|---|---|---|---|---|---|
| 2-28 | H | H | O | CH₃ | (2-iodophenyl, methyl) | 27.93 | 226.3 |
| 2-29 | H | H | O | CH₃ | (2-iodo-5-methyl-4-nitrophenyl) | 848.1 | 48.45 |
| 2-30 | H | H | O | CH₃ | (2-iodo-3-methyl-6-nitrophenyl) | 464.3 | 153.5 |
| 2-31 | H | H | O | CH₃ | (1-methylnaphthalenyl) | 5.696 | 26.56 |
| 2-32(R,S) | H | H | CH₂ | CH₃ | (2-iodo-5-methyl-4-nitrophenyl) | 239.4 (R,S) | 3.411 (R,S) |
| 2-32(R) | H | H | CH₂ | CH₃ | (2-iodo-5-methyl-4-nitrophenyl) | 139.7 (R) | 1.416 (R) |
| 2-32(S) | H | H | CH₂ | CH₃ | (2-iodo-5-methyl-4-nitrophenyl) | 2029 (S) | 160.5 (S) |
| 2-32(R,S) human | H | H | CH₂ | CH₃ | (2-iodo-5-methyl-4-nitrophenyl) |  | 13.60 (R,S), Human |
| 2-32(R) human | H | H | CH₂ | CH₃ | (2-iodo-5-methyl-4-nitrophenyl) |  | 6.668 (R), Human |

TABLE 2-continued
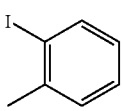
| analog | Z | R | R¹ | R² | A | Ki nM CB1 | Ki nM CB2 |
|---|---|---|---|---|---|---|---|
| 2-33 | H | H | CH₂ | CH₃ | 1-Adamantyl | 11.93 | 4.804 |
| 2-33 human | H | H | CH₂ | CH₃ | 1-Adamantyl | | 2.321 Human |
| 2-34(R,S) | H | H | CH₂ | CH₃ | 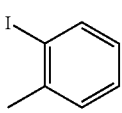 | 2.889 (R,S) | 3.345 (R,S) |
| 2-34(R) | H | H | CH₂ | CH₃ | 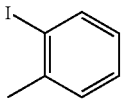 | 1.573 (R) | 1.558 (R) |
| 2-34(S) | H | H | CH₂ | CH₃ | 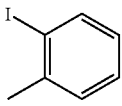 | 14.17 (S) | 6.789 (S) |
| 2-34(R,S) human | H | H | CH₂ | CH₃ | 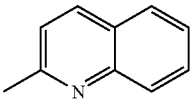 | | 2.488 Human |
| 2-35 | H | H | CH₂ | CH₃ | 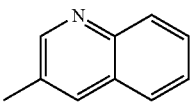 | 14.36 | 20.93 |
| 2-36 | H | H | CH₂ | CH₃ | 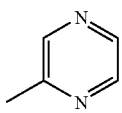 | 133.1 | 8.532 |
| 2-37 | H | H | CH₂ | CH₃ | 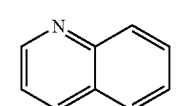 | 3541 | 836.6 |
| 2-38 | H | H | CH₂ | CH₃ | 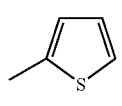 | 719.3 | 747.5 |
| 2-39 | H | H | CH₂ | CH₃ |  | 41.44 | 19.53 |

TABLE 2-continued

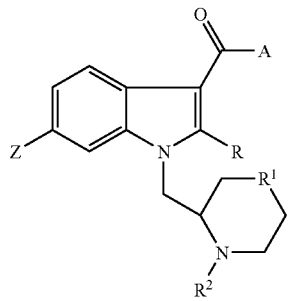

| analog | Z | R | R¹ | R² | A | Ki nM CB1 | Ki nM CB2 |
|---|---|---|---|---|---|---|---|
| 2-40 | H | H | CH₂ | CH₃ | 3-methylisoquinoline | 28.65 | 14.54 |
| 2-41 | H | H | CH₂ | CH₃ | 2-methylquinoxaline | 157.8 | 159.7 |
| 2-42 | H | H | CH₂ | CH₃ | 2-methylpyridine | 421.4 | 147.2 |
| 2-43 | H | H | CH₂ | CH₃ | 2-methylpyridine N-oxide | 8816 | 1858 |
| 2-44 | H | H | CH₂ | CH₃ | 4-methylisoquinoline | 16.94 | 7.037 |
| 2-45 | H | H | CH₂ | CH₃ | 4-iodo-3-methylbenzonitrile | 418.5 | 15.82 |
| 2-46 | H | H | CH₂ | CH₃ | 4-iodo-3-methylbenzonitrile Hydrochloride | 338.7 | 15.41 |
| 2-47 | H | H | CH₂ | CH₃ | 4-iodo-3-methylbenzoic acid Hydrochloride | 240.2 | 18.76 |
| 2-48 | H | H | CH₂ | CH₃ | 4-iodo-3-methylbenzamide | 390.0 | 47.17 |

TABLE 2-continued

![structure: indole-3-carbonyl-A with Z at 6-position, R at 2-position, N-CH2-piperidine(R1)-N-R2]

| analog | Z | R | R¹ | R² | A | Ki nM CB1 | Ki nM CB2 |
|---|---|---|---|---|---|---|---|
| 2-49 | H | H | CH₂ | CH₃ | 4-iodo-3-methyl-phenol | 29.07 | 18.63 |
| 2-50 | H | H | CH₂ | CH₃ | 4-iodo-3-methyl-aniline | | |
| 2-51 | H | H | CH₂ | CH₃ | N-(4-iodo-3-methylphenyl)acetamide | | |
| 2-52 | H | H | CH₂ | CH₃ | N-(4-iodo-3-methylphenyl)trifluoroacetamide | | |
| 2-53 | H | H | CH₂ | CH₃ | N-(4-iodo-3-methylphenyl)methanesulfonamide | | |

Preparation of Compounds:

The above materials were generally prepared following Scheme 1 with the exception that N-methyl-2-piperidinemethyl chloride is used in place of acetoxylalkylhalides for the alkylation of the indole 1-position.

Scheme 1

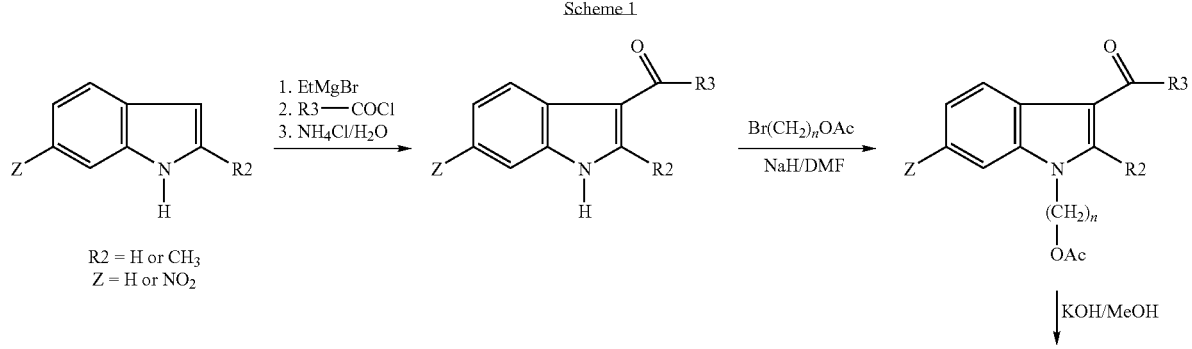

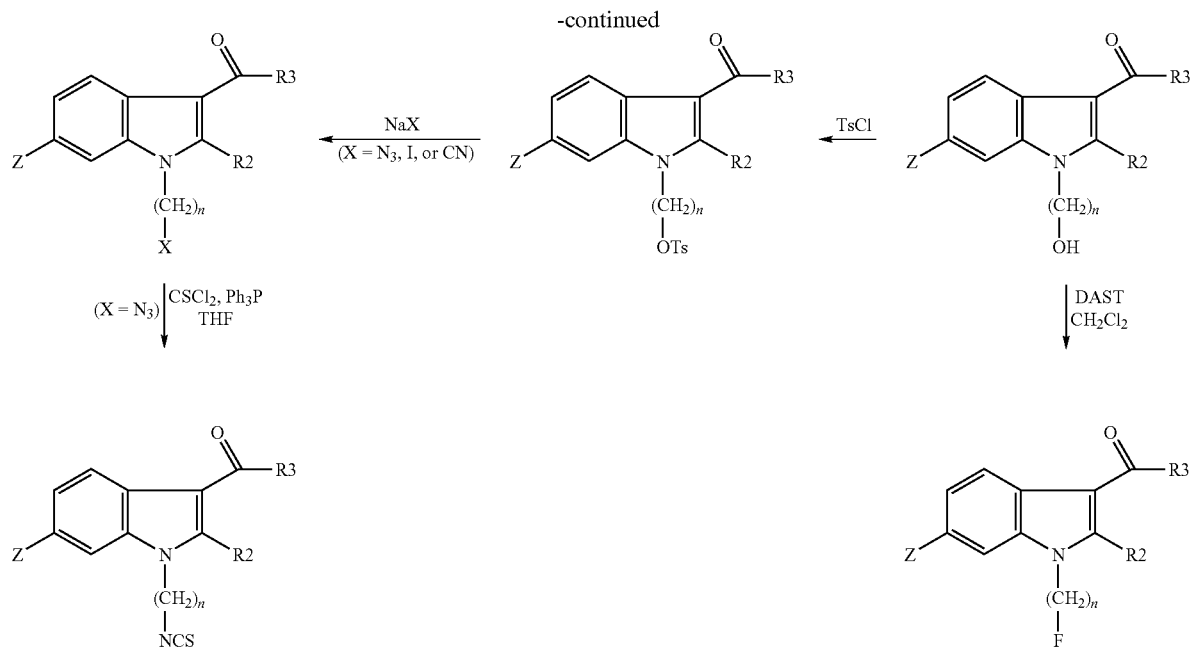

When Z=NO₂, the structures can be transformed to different substituents using methods outlined in Scheme 2.

The commercially unavailable R3-COCl used in Scheme 1 can be prepared according to Scheme 3.

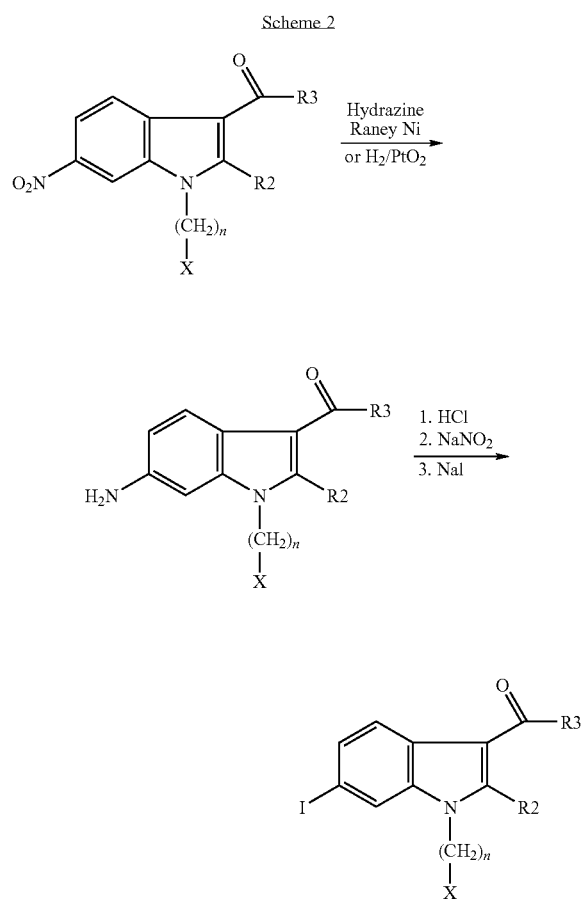

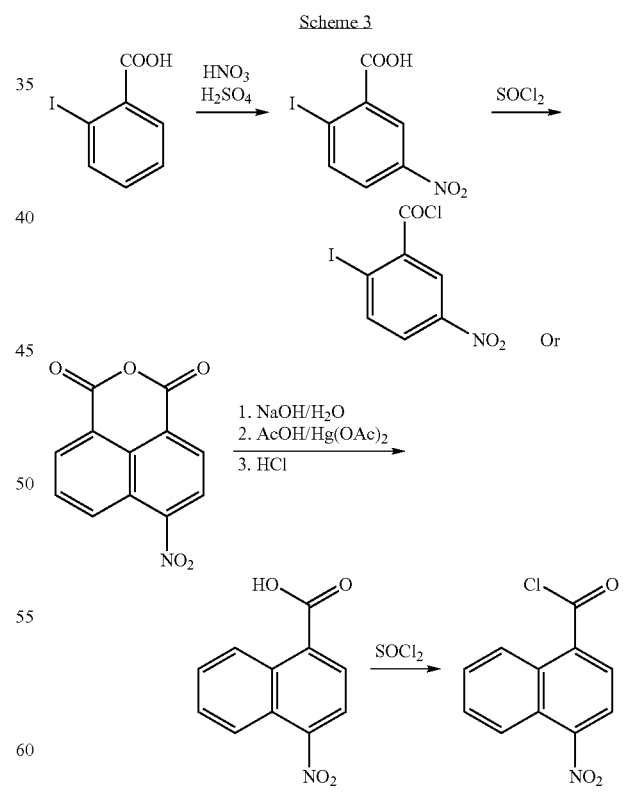

After these acid chlorides are connected at the indole 3-position, the nitro group therein can be further transformed into amino, iodo, azido, and isothiocyanate groups according to the methods outlined in Scheme 4.

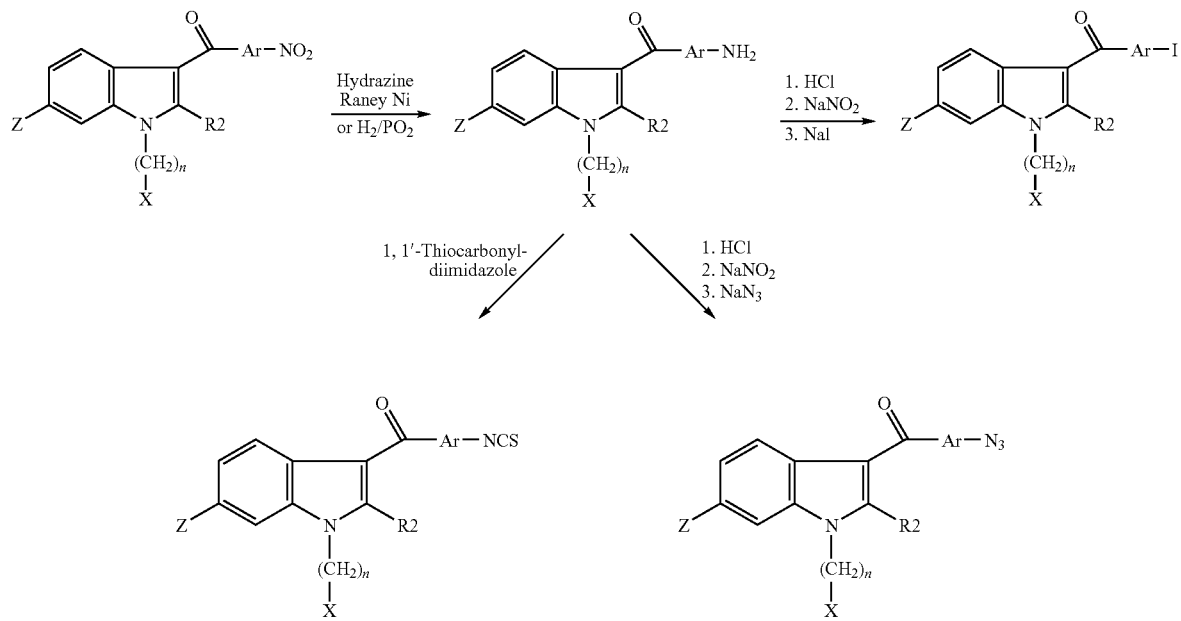

Scheme 4

Examples of specific analogs were prepared as follows:

1-(N-Methyl-2-piperidinyl)methyl-3-(3-quinolinecarbonyl)-1H-indole

To the suspension of 200 mg (1.5 mmol) of anhydrous $AlCl_3$ in 8 ml absolute methylene chloride was added 287.4 mg (1.5 mmol) 3-quinolinecarbonyl chloride in 5 ml methylene chloride and the reaction mixture was stirred 30 min at room 22-25° C. The (N-Methyl-2-piperidinyl)methyl-1H-indole 228.3 mg (1.0 mmol) in 5 ml of methylene chloride was added by dropwise during 1.5 h and the mixture stirred 36 h. The reaction was work-up by addition of 20 ml 2M solution of sodium hydroxide and extracted by ethyl acetate (3×20 ml). The combined extract dried by sodium sulfate. After removing of solvents the rest (0.365 g) was purified by chromatography (silica gel, toluene-triethylamine, 10:1).

1-(N-Methyl-2-piperidinyl)methyl-3-(1-adamantanecarbonyl)-1H-indole

To the stirring solution of the diethyl aluminum chloride (1.5 ml 1 M soln. in hexane, 180.8 mg, 1.5 mmol) in 10 ml absolute methylene chloride was added at room temp. 298.0 mg (1.5 mmol) 1-adamantanecarbonyl chloride in 5 ml of methylene chloride and the reaction mixture was stirred 15 min. The solution of (N-Methyl-2-piperidinyl)methyl-1H-indole (228.3 mg, 1.0 mmol) in 5 ml of methylene chloride was added during 3 min and mixture was stirred and reflux 48 h. The reaction was work-up by addition of 20 ml 2M solution of sodium hydroxide and extracted by ethyl acetate (3×20 ml), washed to times by water and two times by brine. The combined extract dried by the mixture of sodium sulfate and potassium carbonate. After removing of solvents the rest was purified by chromatography (silica gel, methanol ethyl acetate 1:1).

1-(N-Methyl-2-piperidinyl)methyl-3-(2-iodo-5-cyano)benzoyl-1H-indole 1-(N-Methyl-2-piperidinyl)methyl-3-(2-iodo-5-amino)benzoyl-1H-indole (111.6 mg, 0.236 mmol) was dissolved in 3 ml of water containing 43 mg (1.179 mmol) of hydrogen chloride (101 mkl 38% HCl in 3 ml $H_2O$). The this solution was added at stirring sodium nitrite 16.64 mg (0.241 mmol) in 1 ml of water at 0° C. After 1 h the obtained diazonium salt was gradually added to solution of cuprous cyanide (23.5 mg, 0.264 mmol) in sodium cyanide (28.25 mg (0.528 mmol) in 1 ml of water at 60° C. The reaction mixture was diluted by water, extracted ethyl acetate (3×15 ml), dried sodium sulfate and after removing of solvent purified by chromatography (silica gel, methanol-ethyl acetate, 1:2).

A person of ordinary skill in the art, understanding the disclosures for the general preparation and specific preparation examples would know how to modify the disclosed procedures to achieve the above listed analogs.

The prepared cannabinoid compounds were tested for CB2 receptor binding affinity and for CB1 receptor affinity (to determine selectivity for the CB2 receptor). As used herein, "binding affinity" is represented by the $IC_{50}$ value which is the concentration of an analog required to occupy the 50% of the total number (Bmax) of the receptors. The lower the $IC_{50}$ value, the higher the binding affinity. As used herein a compound is said to have "binding selectivity" if it has higher binding affinity for one receptor compared to the other receptor; e.g. a compound that has an $IC_{50}$ of 0.1 nM for CB1 and 10 nM for CB2, is 100 times more selective for the CB1 receptor. The binding affinities ($K_i$) are expressed in nanomoles (nM).

For the CB1 receptor binding studies, membranes were prepared from rat forebrain membranes according to the procedure of P. R. Dodd et al; *A Rapid Method for Preparing Synaptosomes: Comparison with Alternative Procedures,*

Brain Res., 107-118 (1981). The binding of the novel analogues to the CB1 cannabinoid receptor was assessed as described in W. A. Devane et al; *Determination and Characterization of a Cannabinoid Receptor in a Rat Brain*, Mol. Pharmacol., 34, 605-613 (1988) and A. Charalambous et al; "5'-azido Δ⁸-THC: A Novel Photoaffinity Label for the Cannabinoid Receptor", *J. Med. Chem.*, 35, 3076-3079 (1992) with the following changes. The above articles are incorporated by reference herein.

Membranes, previously frozen at −80° C., were thawed on ice. To the stirred suspension was added three volumes of TME (25 mM Tris-HCl buffer, 5 mM $MgCl_2$ and 1 mM EDTA) at a pH 7.4. The suspension was incubated at 4° C. for 30 min. At the end of the incubation, the membranes were pelleted and washed three times with TME.

The treated membranes were subsequently used in the binding assay described below. Approximately 30 μg of membranes were incubated in silanized 96-well microtiter plate with TME containing 0.1% essentially fatty acid-free bovine serum albumin (BSA), 0.8 nM [³H] CP-55,940, and various concentrations of test materials at 30° C. for 1 hour. The samples were immediately filtered using a Packard Filtermate 196 and Whatman GF/C filterplates and washed with wash buffer (TME) containing 0.5% BSA. Radioactivity was detected using MicroScint 20 scintillation cocktail added directly to the dried filterplates, and the filterplates were counted using a Packard Instruments Top-Count. Nonspecific binding was assessed using 100 nM CP-55,940. Data collected from three independent experiments performed with duplicate determinations was normalized between 100% and 0% specific binding for [³H] CP-55,940, determined using buffer and 100 nM CP-55,940. The normalized data was analyzed using a 4-parameter nonlinear logistic equation to yield $IC_{50}$ values. Data from at least two independent experiments performed in duplicate was used to calculate $IC_{50}$ values which were converted to $K_i$ values using the using the assumptions of Cheng et al; "Relationship Between the Inhibition Constant ($K_i$) and the concentration of Inhibitor which causes 50% Inhibition ($IC_{50}$) of an Enzymatic Reaction", *Biochem. Pharmacol.*, 22, 3099-3102, (1973), which is incorporated by reference herein.

For the CB2 receptor binding studies, membranes were prepared from frozen mouse spleen essentially according to the procedure of P. R. Dodd et al; "A Rapid Method for Preparing Synaptosomes: Comparison with Alternative Procedures", *Brain Res.*, 226, 107-118 (1981) which is incorporated by reference herein. Silanized centrifuge tubes were used throughout to minimize receptor loss due to adsorption. The CB2 binding assay was conducted in the same manner as the CB1 binding assay. The binding affinities ($K_i$) were also expressed in nanomoles (nM). The structures, binding affinities and selectivities are summarized in Table 1.

As can be seen from the results in TABLES 1 and 2, some of the compounds, for example, 2-7, show a high selectivity for the CB2 receptor. The compounds described herein have high potential when administered in therapeutically effective amounts for providing a physiological effect useful to treat a variety of disease conditions. Naturally, the disclosure also encompasses any physiologically acceptable salts, diasteromers, enantiomers, double bond isomers and mixtures of the above disclosed compounds.

In addition, some of the iodide and fluoride containing compounds, for example, 2-7 or 2-24, are potential radioactive probes which would be useful for imaging in vivo the distribution of cannabinoid receptors. Further, azido containing compounds would be useful as affinity probes for characterizing binding pockets of cannabinoid receptors.

While preferred embodiments of the foregoing have been set forth for purposes of illustration, the foregoing description should not be deemed a limitation of the disclosure herein. Accordingly, various modifications, adaptations and alternatives may occur to one skilled in the art without departing from the spirit and scope of the present disclosure.

What is claimed is:

1. A compound of formula I, including a physiologically acceptable salt, diasteromer, enantiomer or double bond isomer of formula I:

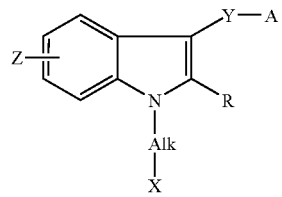

wherein:
   Z is selected from hydrogen, halogen, hydroxy, alkoxy, thioalkoxy, aryl or alkyl;
   Alk is selected from an alkyl group or a substituted alkyl group;
   X is selected from $NHSO_2R^5$, a 5, 6 or 7 member heterocyclic ring, a substituted 5, 6 or 7 member heterocyclic ring, a bicyclic ring or a heterobicyclic ring;
   $R^5$ is selected from alkyl, halogenated alkyl and fluorinated alkyl;
   R is selected from hydrogen, CN, CHO, alkyl, halogenated alkyl, fluorinated alkyl or substituted alkyl;
   Y is selected from C=O, CH=CH (cis or trans), CONH or C=NH; and
   A is selected from alkyl, $COCF_3$, adamantyl, azoadamantyl, cycloalkyl, phenyl, naphthyl, 9-anthracenyl, pyridinyl, quinolinyl, isoquinolinyl, quinazolinyl, an aliphatic bicyclic ring, an azabicyclic ring, a heterobicyclic ring, any of the above with one or more substituents independently selected from amino, halogen, hydroxy, nitro, nitroso, azido, isothiocyanato, cyano, COOH, alkyl, $CONR^3R^4$ (where $R^3$ and $R^4$ are each independently selected from H, alkyl or substituted alkyl), $NCOR^3R^4$ (where $R^3$ and $R^4$ are each independently selected from H, alkyl, substituted alkyl, $CF_3$), $SO_2NR^3R^4$ (where $R^3$ and $R^4$ are each independently selected from H, alkyl, substituted alkyl or $CF_3$); or a salt of any of the above;
wherein at least one atom in the compound is an unnatural isotope.

2. The compound of claim 1 wherein the isotope is radioactive.

3. The compound of claim 1 wherein the isotope is selected from ³H, ¹¹C, ¹³C, ¹⁴C, ¹⁵O, ¹⁸O, ¹⁸F, ⁷⁵Br, ⁷⁶Br, ⁷⁷Br, ⁸²Br, ¹²⁵I, or ¹³¹I.

4. The compound of claim 1 wherein the isotope a halogen isotope.

5. The compound of claim 1 wherein the isotope is a halogen isotope selected from ¹⁸F, ⁷⁵Br, ⁷⁶Br, ⁷⁷Br, ⁸²Br, ¹²⁵I, or ¹³¹I.

6. The compound of claim 1 wherein:
   Z is hydrogen;
   Alk is a $C_{1-2}$ alkyl group;
   X is selected from a 5, 6 or 7 member heterocyclic ring, a substituted 5, 6 or 7 member heterocyclic ring, a bicyclic ring; or a bicyclic ring including at least one heterobicyclic ring;

R is hydrogen;
Y is carbonyl; and
A is selected from alkyl, COCF$_3$, adamantyl, azoadamantyl, cycloalkyl, phenyl, naphthyl, 9-anthracenyl, pyridinyl, quinolinyl, isoquinolinyl, quinazolinyl, an aliphatic bicyclic ring, an azabicyclic ring, any of the above with one or more substituents independently selected from amino, halogen, hydroxy, nitro, nitroso, azido, isothiocyanato, cyano, COOH, alkyl, CONR$^3$R$^4$ (where R$^3$ and R$^4$ are each independently selected from H, alkyl or substituted alkyl), NCOR$^3$R$^4$ (where R$^3$ and R$^4$ are each independently selected from H, alkyl, substituted alkyl, CF$_3$), SO$_2$NR$^3$R$^4$ (where R$^3$ and R$^4$ are each independently selected from H, alkyl, substituted alkyl or CF$_3$), or a salt of any of the above.

7. The compound of claim 1 having the following structure,

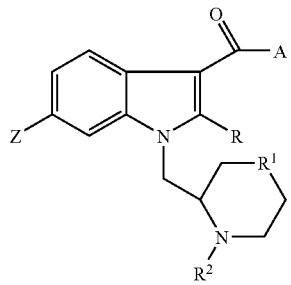

wherein:
Z is hydrogen;
R is hydrogen;
R$^1$ is selected from N, O, S or CH$_2$;
R$^2$ is selected from H, alkyl, CF$_3$, CH$_2$C≡CH, CH$_2$CH═CH$_2$ or CH$_2$Ph; and
A is selected from alkyl, COCF$_3$, adamantyl, azoadamantyl, cycloalkyl, phenyl, naphthyl, 9-anthracenyl, pyridinyl, quinolinyl, isoquinolinyl, quinazolinyl, an aliphatic bicyclic ring, an azabicyclic ring, any of the above with one or more substituents independently selected from amino, halogen, hydroxy, nitro, nitroso, azido, isothiocyanato, cyano, COOH, alkyl, CONR$^3$R$^4$ (where R$^3$ and R$^4$ are each independently selected from H, alkyl or substituted alkyl), NCOR$^3$R$^4$ (where R$^3$ and R$^4$ are each independently selected from H, alkyl, substituted alkyl, CF$_3$), SO$_2$NR$^3$R$^4$ (where R$^3$ and R$^4$ are each independently selected from H, alkyl, substituted alkyl or CF$_3$), or a salt of any of the above.

8. A radiopharmaceutical composition comprising a compound of formula I, including a physiologically acceptable salt, diasteromer, enantiomer or double bond isomer of formula I:

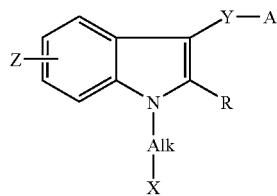

wherein:
Z is selected from hydrogen, halogen, hydroxy, alkoxy, thioalkoxy, aryl or alkyl;
Alk is selected from an alkyl group or a substituted alkyl group;
X is selected from NHSO$_2$R$^5$, a 5, 6 or 7 member heterocyclic ring, a substituted 5, 6 or 7 member heterocyclic ring, a bicyclic ring or a heterobicyclic ring;
R$^5$ is selected from alkyl, halogenated alkyl and fluorinated alkyl;
R is selected from hydrogen, CN, CHO, alkyl, halogenated alkyl, fluorinated alkyl or substituted alkyl;
Y is selected from C═O, CH═CH (cis or trans), CONH or C═NH; and
A is selected from alkyl, COCF$_3$, adamantyl, azoadamantyl, cycloalkyl, phenyl, naphthyl, 9-anthracenyl, pyridinyl, quinolinyl, isoquinolinyl, quinazolinyl, an aliphatic bicyclic ring, an azabicyclic ring, a heterobicyclic ring, any of the above with one or more substituents independently selected from amino, halogen, hydroxy, nitro, nitroso, azido, isothiocyanato, cyano, COOH, alkyl, CONR$^3$R$^4$ (where R$^3$ and R$^4$ are each independently selected from H, alkyl or substituted alkyl), NCOR$^3$R$^4$ (where R$^3$ and R$^4$ are each independently selected from H, alkyl, substituted alkyl, CF$_3$), SO$_2$NR$^3$R$^4$ (where R$^3$ and R$^4$ are each independently selected from H, alkyl, substituted alkyl or CF$_3$); or a salt of any of the above;
wherein at least one atom in the compound is an unnatural isotope; and
a pharmaceutically acceptable carrier or a pharmaceutically acceptable excipient.

9. The radiopharmaceutical composition of claim 8 wherein the isotope is radioactive.

10. The radiopharmaceutical composition of claim 8 wherein the isotope is selected from $^3$H, $^{11}$C, $^{13}$C, $^{14}$C, $^{15}$O, $^{18}$O, $^{18}$F, $^{75}$Br, $^{76}$Br, $^{77}$Br, $^{82}$Br, $^{125}$I, or $^{131}$I.

11. The radiopharmaceutical composition of claim 8 wherein the isotope a halogen isotope.

12. The radiopharmaceutical composition of claim 8 wherein the isotope is a halogen isotope selected from $^{18}$F, $^{75}$Br, $^{76}$Br, $^{77}$Br, $^{82}$Br, $^{125}$I, or $^{131}$I.

13. A method of radioactive imaging in an individual or animal, comprising:
administering to the individual or animal a pharmacological composition comprising a compound of formula I, including a physiologically acceptable salt, diasteromer, enantiomer or double bond isomer of formula I:

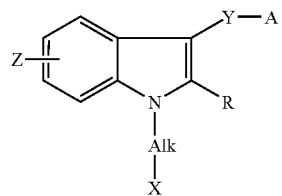

wherein:
Z is selected from hydrogen, halogen, hydroxy, alkoxy, thioalkoxy, aryl or alkyl;
Alk is selected from an alkyl group or a substituted alkyl group;
X is selected from NHSO$_2$R$^5$, a 5, 6 or 7 member heterocyclic ring, a substituted 5, 6 or 7 member heterocyclic ring, a bicyclic ring or a heterobicyclic ring;
R$^5$ is selected from alkyl, halogenated alkyl and fluorinated alkyl;
R is selected from hydrogen, CN, CHO, alkyl, halogenated alkyl, fluorinated alkyl or substituted alkyl;
Y is selected from C═O, CH═CH (cis or trans), CONH or C═NH;

A is selected from alkyl, COCF$_3$, adamantyl, azoadamantyl, cycloalkyl, phenyl, naphthyl, 9-anthracenyl, pyridinyl, quinolinyl, isoquinolinyl, quinazolinyl, an aliphatic bicyclic ring, an azabicyclic ring, a heterobicyclic ring, any of the above with one or more substituents independently selected from amino, halogen, hydroxy, nitro, nitroso, azido, isothiocyanato, cyano, COOH, alkyl, CONR$^3$R$^4$ (where R$^3$ and R$^4$ are each independently selected from H, alkyl or substituted alkyl), NCOR$^3$R$^4$ (where R$^3$ and R$^4$ are each independently selected from H, alkyl, substituted alkyl, CF$_3$), SO$_2$NR$^3$R$^4$ (where R$^3$ and R$^4$ are each independently selected from H, alkyl, substituted alkyl or CF$_3$); or a salt of any of the above;

wherein at least one atom in the compound is a radioactive isotope;

allowing the compound to bind to a cannabinoid receptor; and detecting energy emitted by the radioactive isotope.

14. The method of claim 13 wherein the compound is administered to an individual.

15. The method of claim 13 wherein the step of detecting comprises measuring the distribution of compound within the individual or animal using positron emission tomography or single photon emission computed tomography.

16. The method of claim 13 wherein the isotope is selected from $^3$H, $^{11}$C, $^{13}$C, $^{14}$C, $^{15}$O, $^{18}$O, $^{18}$F, $^{75}$Br, $^{76}$Br, $^{77}$Br, $^{82}$Br, $^{125}$I, or $^{131}$I.

17. The method of claim 13 wherein the isotope a halogen isotope.

18. The method of claim 13 wherein the isotope is a halogen isotope selected from $^{18}$F, $^{75}$Br, $^{76}$Br, $^{77}$Br, $^{82}$Br, $^{125}$I, or $^{131}$I.

19. The method of claim 13 wherein in the compound:
Z is hydrogen;
Alk is a C$_{1-2}$alkyl group;
X is selected from a 5, 6 or 7 member heterocyclic ring, a substituted 5, 6 or 7 member heterocyclic ring, a bicyclic ring; or a heterobicyclic ring;
R is hydrogen;
Y is carbonyl; and
A is selected from alkyl, COCF$_3$, adamantyl, azoadamantyl, cycloalkyl, phenyl, naphthyl, 9-anthracenyl, pyridinyl, quinolinyl, isoquinolinyl, quinazolinyl, an aliphatic bicyclic ring, an azabicyclic ring, any of the above with one or more substituents independently selected from amino, halogen, hydroxy, nitro, nitroso, azido, isothiocyanato, cyano, COOH, alkyl, CONR$^3$R$^4$ (where R$^3$ and R$^4$ are each independently selected from H, alkyl or substituted alkyl), NCOR$^3$R$^4$ (where R$^3$ and R$^4$ are each independently selected from H, alkyl, substituted alkyl, CF$_3$), SO$_2$NR$^3$R$^4$ (where R$^3$ and R$^4$ are each independently selected from H, alkyl, substituted alkyl or CF$_3$), or a salt of any of the above.

20. The method of claim 13 wherein the compound has the following structure,

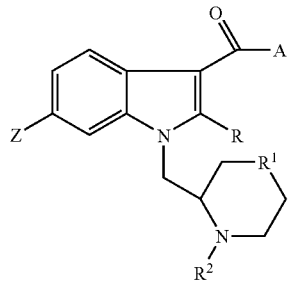

wherein:
Z is hydrogen;
R is hydrogen;
R$^1$ is selected from N, O, S or CH$_2$;
R$^2$ is selected from H, alkyl, CF$_3$, CH$_2$C≡CH, CH$_2$CH=CH$_2$ or CH$_2$Ph; and
A is selected from alkyl, COCF$_3$, adamantyl, azoadamantyl, cycloalkyl, phenyl, naphthyl, 9-anthracenyl, pyridinyl, quinolinyl, isoquinolinyl, quinazolinyl, an aliphatic bicyclic ring, an azabicyclic ring, any of the above with one or more substituents independently selected from amino, halogen, hydroxy, nitro, nitroso, azido, isothiocyanato, cyano, COOH, alkyl, CONR$^3$R$^4$ (where R$^3$ and R$^4$ are each independently selected from H, alkyl or substituted alkyl), NCOR$^3$R$^4$ (where R$^3$ and R$^4$ are each independently selected from H, alkyl, substituted alkyl, CF$_3$), SO$_2$NR$^3$R$^4$ (where R$^3$ and R$^4$ are each independently selected from H, alkyl, substituted alkyl or CF$_3$), or a salt of any of the above.

* * * * *

UNITED STATES PATENT AND TRADEMARK OFFICE
CERTIFICATE OF CORRECTION

| | | |
|---|---|---|
| PATENT NO. | : 7,820,144 B2 | Page 1 of 1 |
| APPLICATION NO. | : 11/620248 | |
| DATED | : October 26, 2010 | |
| INVENTOR(S) | : Makriyannis et al. | |

It is certified that error appears in the above-identified patent and that said Letters Patent is hereby corrected as shown below:

Column 24:

Line 66, delete "bicyclic ring including at least one"

Signed and Sealed this

Seventh Day of August, 2012

David J. Kappos
*Director of the United States Patent and Trademark Office*